United States Patent [19]

Dennis

[11] 4,263,287

[45] Apr. 21, 1981

[54] FENVALERATE-PHOSMET INSECTICIDAL COMPOSITION

[75] Inventor: Stephan Dennis, Marlboro, N.J.

[73] Assignee: Stauffer Chemical Company, Richmond, Calif.

[21] Appl. No.: 90,782

[22] Filed: Nov. 2, 1979

[51] Int. Cl.³ .................... A01N 37/34; A01N 57/00; A01N 57/26
[52] U.S. Cl. ..................................... 424/200; 424/304
[58] Field of Search ................................ 424/200, 304

[56] References Cited

U.S. PATENT DOCUMENTS

| 3,457,283 | 7/1969 | Szabo et al. | 424/200 |
| 3,839,562 | 10/1974 | Chodnekar et al. | 424/200 |
| 3,846,547 | 11/1974 | Freiberg et al. | 424/200 |
| 4,087,523 | 5/1978 | Lovell | 424/200 |
| 4,144,331 | 3/1979 | Felton et al. | 424/219 |

FOREIGN PATENT DOCUMENTS

| 724191 | 12/1965 | Canada | 424/200 |
| 2757768 | 6/1978 | Fed. Rep. of Germany | 424/304 |
| 7209507 | 1/1973 | Netherlands | 424/200 |
| 78/0712 | 2/1978 | South Africa | 424/200 |

OTHER PUBLICATIONS

Chem. Abst. 80 120746(w) (1974), Sumitonio Chem. Co. Ltd.
Chem. Abst. 84 30686(e) (1976)—Fujunoto et al.
Chem. Abst. 85 94107(v) (1976)—Ono et al.

*Primary Examiner*—Douglas W. Robinson
*Attorney, Agent, or Firm*—Joel G. Ackerman

[57] ABSTRACT

A mixture of the insecticides fenvalerate and phosmet in a weight ratio of from 20:1 to 100:1 has been found to produce synergistic insecticidal effect, particularly against the Colorado potato beetle.

7 Claims, No Drawings

FENVALERATE-PHOSMET INSECTICIDAL COMPOSITION

BACKGROUND AND PRIOR ART

This application relates to a new and unexpectedly synergistic insecticidal composition containing the commercial insecticides fenvalerate and phosmet, and particularly containing these compounds in a weight ratio of from about 20:1 to about 100:1, and formulated for application at a rate of 0.5 to 1.0 lb./acre (0.6 to 1.12 kg./ha) phosmet and 0.01 to 0.025 lb./acre (0.0112 to 0.28 kg./ha) fenvalerate. Rates of application as given herein are expressed in pounds of the active ingredient or ingredients (a.i.) per acre and the equivalent in kilograms a.i. per hectare.

Fenvalerate is the generic name of the commercial insecticide cyano(3-phenoxyphenyl)methyl-4-chloro-alpha-(1-methylethyl)benzene-acetate, which has the formula

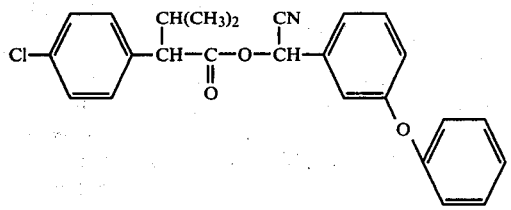

and is sold under serveral trademarks, including the registered trademarks Pydrin and Sumicidin. Phosmet, or N-(mercaptomethyl) phthalimide S-(O,O-dimethylphosphorodithioate) which has the formula

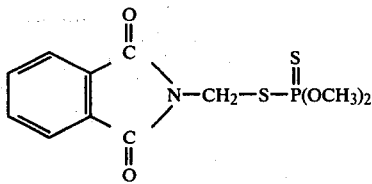

is a commercial insecticide which is sold under several trademarks including the registered trademarks Imidan and Prolate.

Phosmet in particular has been in commercial use for some years and has been registered for use against a number of insects. Included among these insects are three which attack potatoes: the Colorado potato beetle, the potato flea beetle and the potato leafhopper. Registration information for use against these insects directs the application of phosmet at a rate of 2 lb./acre (equivalent to 2.24 kg./ha). Recently, however, some resistance has been shown to phosmet by these insects, particularly in certain areas of the eastern United States. The invention as described above however, appears to provide protection against the Colorado potato beetle utilizing application rates of phosmet of less then 2 lb./acre in combination with fenvalerate in the amounts indicated. Synergistic results have been obtained utilizing mixtures of phosmet and fenvalerate at weight ratios of from 20:1 to 100:1 (with a weight ratio of 50:1 being particularly preferred both for technical and economic reasons) and which is applied to a locus to be treated at a rate of 0.5 to 1.0 lb./acre (0.6–1.12 kg./ha) phosmet and 0.01 to 0.025 lb/acre (0.0112–0.028 kg./ha) fenvalerate.

Results obtained from the testing of such mixtures are described below.

FIELD TEST—SPRING/SUMMER SEASON:

Tests were conducted in a location in the Virginia section of the Delmarva Penninsula.

Norchip variety Irish potatoes were planted at the end of March in 3-foot (0.91 m.) rows with 12-inch (0.30 m.) spacing, with infestations of the Colorado potato beetle (Leptinotarsa decemlineata) occuring after planting. On the following June 1, 11, 19, 26 and 30th, four replications, each being one row 25 ft. (7.5 m) long were sprayed with an aqueous solution of the active ingredients at the rates and weight ratios indicated in the following Table 1. A count of potato beetle larvae, which is the form which causes damage to potato crops, was taken on June 7th by counting the larvae above ground on ten hills on each row. On June 20, June 29th and July 7th, ratings were taken on injury to the foilage caused by the larvae, using a scale of from 0 to 5 with 0 being equivalent to no damage from the larvae and a rating of 5 equivalent to nearly total defoliation. On July 26th, the yield of pounds of potatoes per 25 foot plot was determined. Simultaneously with the testing above, a check plot of the same potatoes planted at the same time, was permitted to become infested with the potato beetle and was not treated.

The active ingredients were applied to adjacent rows of potatoes as follows:
phosmet alone—0.5 and 1.0 lbs./acre
fenvalerate alone—0.01, 0.025, 0.05 and 0.1 lbs./acre
phosmet/fenvalerate mixtures—ratios of 0.5:0.01, 0.5:0.025, 1.0:0.01 and 1.0:0.025 lbs./acre.

The phosmet was used in the form of a wettable powder containing approximately 50% by weight phosmet. The fenvalerate was utilized in the form of an emulsion containing approximately 2.4 lbs./gal. Sprays were prepared by the usual tank mixing techniques with either the wettable powder, emulsion or mixtures thereof, with the active ingredient being dissolved in water to obtain a sprayable solution which was applied at a rate of 100 gallons of water per acre. Ten days before planting the potatoes, the ground was fertilized with 10—1-0—10 fertilizer applied at a rate of 1100 lbs./acre. On April 18th, the herbicide metribuzin[4-amino-6-(1,1-dimethylethyl)-3-methylthio-1,2,4-triazin-5(4H)-one] was applied at a rate of 1¼ lb./acre. These are practices customarily followed by growers in this area.

The results of these experiments are given in the following Table 1. Values for insect control have been converted to percent control by comparison with the untreated check plot, on which was found 323.8 insects per 10 plants.

TABLE 1

| Insecticide lb./acre | % Control of potato beetle 6/7 | Foliage injury rating 6/20 | 6/29 | 7/7 | potato yield, lb./plot |
|---|---|---|---|---|---|
| Phosmet, 0.5 | 63.3 | 3.8 | 4.5 | 4.8 | 32.3 |
| Phosmet, 1.0 | 91.7 | 2.5 | 3.6 | 4.4 | 40.5 |
| Fenvalerate, 0.01 | 50.2 | 4.1 | 4.6 | Def. | 31.0 |
| Fenvalerate, 0.025 | 85.8 | 3.7 | 4.1 | 4.4 | 40.8 |
| Fenvalerate, 0.05 | 96.9 | 2.0 | 2.5 | 3.1 | 57.0 |
| Fenvalerate, 0.1 | 99.8 | 1.4 | 1.7 | 1.9 | 52.8 |
| Phosmet, 0.5 + fenvalerate, 0.01 | 98.9 | 2.4 | 2.5 | 3.0 | 52.8 |
| Phosmet, 0.5 + fenvalerate, 0.025 | 99.5 | 1.8 | 2.3 | 2.7 | 56.5 |

TABLE 1-continued

| Insecticide lb./acre | % Control of potato beetle 6/7 | Foliage injury rating 6/20 | 6/29 | 7/7 | potato yield, lb./plot |
|---|---|---|---|---|---|
| Phosmet, 1.0 + fenvalerate, 0.01 | 98.4 | 1.7 | 2.3 | 2.8 | 58.5 |
| Phosmet, 1.0 + fenvalerate, 0.025 | 99.5 | 1.4 | 1.9 | 2.2 | 58.5 |
| Check (untreated) | 0 | Def. | Def. | Def. | 20.0 |

Def. - Complete defoliation

TEST TWO—SUMMER/AUTUMN:

Similar tests of the two insecticides and mixtures thereof, applied at the same rates were conducted later in the same year, on Pungo size B potatoes, which were planted in 3 foot (0.75 m) rows on July 24th. Infestations of three insects, the Colorado potato beetle, beet armyworm (*Spodoptera exigua*) and leaf miner (Liriomyza sp.) developed. The plots were treated with the insecticide on nine occasions between the following August 21 and October 26 by spraying aqueous solutions of the insecticides at a rate of 100 gallons of water per acre (998 lit./ha.) onto each of four replications. On August 31st, a count of Colorado potato beetle larvae was taken as in Test 1. Counts of beet armyworm and leaf miner larvae were similarly taken on October 4th. The yield of potatoes in cwt/acre was determined on November 14th.

The results of these tests are contained in Table 2. Values for insect control have been converted to percent control by comparison with the untreated check plot, on which were found 202.8 potato beetles, 87 beet armyworms and 156 leaf miners per 10 plants.

TABLE 2

| Insecticide lb./acre | Potato beetle larvae (8/31) | % Control Beet army-worms (10/4 | Leaf-miners (10/4) | Potato Yield, Cwt./ acre (11/14) |
|---|---|---|---|---|
| Phosmet, 0.5 | 90.4 | 58.6 | 43.9 | 87 |
| Phosmet, 1.0 | 96.3 | 60 | 45.3 | 89 |
| Fenvalerate, 0.01 | 70.9 | 56.3 | 32.7 | 74 |
| Fenvalerate, 0.025 | 87.5 | 80 | 49 | 82 |
| Fenvalerate, 0.05 | 99.7 | 93.9 | 84.2 | 103 |
| Fenvalerate, 0.1 | 99.7 | 99 | 92.7 | 112 |
| Phosmet, 0.5 + fenvalerate, 0.01 | 98.0 | 85.8 | 55.6 | 112 |
| Phosmet, 0.5 + fenvalerate, 0.025 | 100 | 90.2 | 84.9 | 107 |
| Phosmet, 1.0 + fenvalerate, 0.01 | 99.9 | 85.1 | 54.9 | 108 |
| Phosmet, 1.0 + fenvalerate, 0.025 | 99.0 | 89.9 | 78.6 | 104 |
| Check (untreated) | 0 | 0 | 0 | 44 |

From the data in Tables 1 and 2, showing the performance of the individual insecticides, the control expected to result from their combination (at the same rates of application) was determined using Limpel's formula:

$$\text{expected result} = X + Y - \frac{XY}{100}$$

(% control)

where
X = control obtained by use of phosmet
Y = control obtained by use of fenvalerate Tables 3 and 4 show the comparison of the expected control for the combinations (calculated as above) with that actually observed. As can be seen from this data, the combinations of these two insecticides generally performed in excess of that which would have been expected from their performance when applied separately at the same rates of application as in the combinations. Particularly effective was the combination of 0.5 lbs./acre phosmet plus 0.01 lbs./acre fenvalerate (or a 50:1 weight ratio). This combination resulted in insect control and potato yield which was equivalent to that obtained by the use of fenvalerate, a quite expensive insecticide alone, at much higher levels of 0.05 and 0.1 lb./acre (see Tables 1 and 2).

TABLE 3

(Spring/Summer Season)
Insect: Colorado Potato beetle

| Insectide lb./acre | % Control observed | % Control expected |
|---|---|---|
| Phosmet, 0.5 | 63.3 | |
| Phosmet, 1.0 | 91.7 | |
| Fenvalerate, 0.01 | 50.2 | |
| Fenvalerate, 0.025 | 85.8 | |
| Phosmet, 0.5 + fenvalerate, 0.01 | 98.9 | 81.8 |
| Phosmet, 0.5 + fenvalerate, 0.025 | 99.5 | 94.8 |
| Phosmet, 1.0 + fenvalerate, 0.01 | 98.4 | 85.9 |
| Phosmet, 1.0 + fenvalerate, 0.025 | 99.5 | 98.8 |

TABLE 4

(Summer/Autumn)

| Insecticide, lb./acre | Potato beetle % control | | Beet armyworm % control | | Leaf miner % control | |
|---|---|---|---|---|---|---|
| | observed | expected | observed | expected | observed | expected |
| Phosmet, 0.5 | 90.4 | | 58.6 | | 43.9 | |
| Phosmet, 1.0 | 96.3 | | 60 | | 45.3 | |
| Fenvalerate, 0.01 | 70.9 | | 56.3 | | 32.7 | |
| Fenvalerate, 0.025 | 87.5 | | 80 | | 49 | |
| Phosmet, 0.5 + fenvalerate, 0.01 | 98.0 | 97.2 | 85.5 | 81.9 | 55.6 | 62.2 |
| Phosmet, 0.5 + fenvalerate, 0.025 | 100 | 98.8 | 90.2 | 91.7 | 84.9 | 71.4 |
| Phosmet, 1.0 + fenvalerate, 0.01 | 99.9 | 98.9 | 85.1 | 82.5 | 54.9 | 63.2 |
| Phosmet, 1.0 + fenvalerate, 0.025 | 99.0 | 99.5 | 89.9 | 92 | 78.6 | 72.1 |

While the experiments were conducted utilizing phosmet in the form of a wettable powder, and fenvalerate in the form of an emulsion, various physical forms of the two insecticides may be utilized to produce the synergistic mixtures claimed herein. The compositions or formulations including the two insecticides described herein may take and be used in any one of a number of solid or liquid forms. Even a mixture of the pure compounds could be used as an insecticide. However, in general, such insecticides are first formulated with one or more inert (i.e. plant compatible or herbicidally inert) carriers or diluents suitable for insecticidal use, before being applied.

Solid forms of compositions containing the insecticide could be, for instance, dusts, granules, tablets, powders and the like. Liquid forms could be, for instance, emulsions, solutions, suspensions, emulsifiable concentrates, flowables and pastes. Such solid and liquid compositions, in addition to the active compound, would contain various carriers or diluents, surface-active agents, solvents, adhesives, thickeners, binders, anti-foaming agents and other substances. Solid carriers or diluents included in certain compositions or formulations may include, for instance, ground natural minerals, such as kaolins, alumina, calcium carbonates, silica, kieselguhr, clay, etc.; ground synthetic minerals such silicates and aluminosilicates, and ground vegetable products such as bark, cornmeal, sawdust, cellulose powder and the like.

It is possible to use highly concentrated liquid compositions containing up to about 95% by weight of the active ingredients, or even the pure compounds alone, when applying them in the form of a finely divided liquid by use of various atomizing equipment such as airplane crop sprayers. For other purposes, however, the various types of compositions which can be utilized for these compounds will contain varying amounts of the compound according to the type of composition and intended use.

In general, compositions may contain from 5 to 95% by weight of the active compounds, more preferably 10 to 85%. Some typical compositions will contain active compounds as follows: wettable powders: 25–80% by weight; oil suspensions, emulsions, solutions and emulsifiable concentrates: 20–80% by weight; aqueous suspensions: 20–50% by weight; dusts and powders: 5 to 20% by weight; granules and pellets: 5 to 20% by weight.

In addition to the active compounds and the various formulating agents, compositions containing these compounds may also contain one or more other active pesticidal agents such as herbicides, fungicides, insecticides, acaricides, nematocides, bactericides and plant growth regulators. Such compositions may also contain soil disinfectants or fumigants and may further contain fertilizers, thus making it possible to provide multi-purpose compositions containing mixtures of phosmet and fenvalerate, as well as optionally other pesticides and also fertilizers, all intended and formulated for use at the same locus.

To control insect pests using the inventive mixture a composition containing an insecticidally effective amount of such mixture is applied to the insect, to a locus at which the insecticidal control is desired, or to food sources (including seeds) on which the insects feed. Thus control may be achieved by direct application of the phosmet/fenvalerate mixture to the insect and/or indirectly by application of the mixture to the locus to be protected such as crops or crop land, to a source of food for insects or to other insect habitats such as breeding or swarming areas. The rate of application of the active ingredients and the concentration applied will vary according to whether it is being directly or indirectly applied to control the insect. In the cases of application to a crop area, depending on the nature of the insect to be controlled and the plant environment the application rate will generally vary from 0.01 to about 2, preferably from about 0.5 to about 2 lbs./acre.

Compositions containing the phosmet/fenvalerate mixture may be applied in any convenient manner. When used in connection with crop or plant protection, application of the mixture may be performed in a preventive (i.e. before infestation) or eradicative (i.e. after infestation) manner. Thus, various compositions containing the mixture of the ingredients can be applied by the use of power dusters, boom and hand sprayers, spray dusters or airplane crop dusters or sprayers. Compositions containing the mixture of the ingredients may also be applied by addition to irrigation waters supplied to the fields to be treated.

What is claimed is:

1. An insecticidal composition comprising insecticidal amounts of phosmet and fenvalerate in a weight ratio of phosmet:fenvalerate of between 20:1 and 100:1.

2. A composition according to claim 1 in which the weight ratio is 50:1.

3. A method for controlling undesirable insects by applying to the insect, the locus thereof or a locus to be protected, an insecticidal composition comprising phosmet and fenvalerate in a weight ratio of from 20:1 to 100:1.

4. A method according to claim 3 in which the mixture is applied so as to provide phosmet at a rate of 0.5 to 1 lb./acre and fenvalerate at a rate of 0.01 to 0.025 lb./acre.

5. A method according to claim 3 in which the phosmet:fenvalerate weight ratio is 50:1.

6. A method according to claim 3 in which the phosmet is applied at a rate of 0.5 lb./acre and fenvalerate at a rato of 0.01 lb./acre.

7. A method according to claim 3 in which the insect to be controlled is the Colorado potato beetle.

* * * * *

UNITED STATES PATENT AND TRADEMARK OFFICE
CERTIFICATE OF CORRECTION

PATENT NO. : 4,263,287
DATED : April 21, 1981
INVENTOR(S) : Stephan Dennis

It is certified that error appears in the above-identified patent and that said Letters Patent are hereby corrected as shown below:

Table 4, under the heading Insecticide, lb./acre, line 9, please add 0.01 after the word fenvalerate.

Signed and Sealed this

Twentieth Day of October 1981

[SEAL]

Attest:

GERALD J. MOSSINGHOFF

Attesting Officer   Commissioner of Patents and Trademarks